United States Patent [19]

Inaba et al.

[11] Patent Number: 4,752,647

[45] Date of Patent: Jun. 21, 1988

[54] PROCESS FOR PRODUCING A TETRAALKOXYSILANE

[75] Inventors: Shinichi Inaba; Shuichi Honda; Kohji Koga, all of Minamata, Japan

[73] Assignee: Chisso Corporation, Ohsaka, Japan

[21] Appl. No.: 932,315

[22] Filed: Nov. 19, 1986

[30] Foreign Application Priority Data

Nov. 20, 1985 [JP] Japan ................................. 60-260368

[51] Int. Cl.$^4$ ................................................ C07F 7/04
[52] U.S. Cl. ...................................................... 556/470
[58] Field of Search ......................................... 556/470

[56] References Cited

U.S. PATENT DOCUMENTS

| 4,113,761 | 9/1978 | Kreuzburg et al. | 556/470 |
| 4,197,252 | 4/1980 | Joch et al. | 556/446 |
| 4,224,234 | 9/1980 | Flick et al. | 556/472 |
| 4,288,604 | 9/1981 | Magee et al. | 556/470 |

FOREIGN PATENT DOCUMENTS

| 2816386 | 10/1979 | Fed. Rep. of Germany | 556/470 |
| 2354683 | 11/1982 | Fed. Rep. of Germany | 556/470 |
| 2249890 | 5/1975 | France | 556/470 |
| 2332993 | 6/1977 | France | 556/470 |
| 2422670 | 9/1979 | France | 556/470 |
| 45-8217 | 3/1970 | Japan | 556/470 |
| 50-71632 | 6/1975 | Japan | 556/470 |
| 54-138523 | 10/1979 | Japan | 556/470 |
| 55-149290 | 11/1980 | Japan | 556/470 |
| 61-1693 | 7/1986 | Japan | 556/470 |

*Primary Examiner*—Paul F. Shaver
*Attorney, Agent, or Firm*—Leydig, Voit & Mayer

[57] ABSTRACT

A process for producing a tetraalkoxysilane by subjecting silicon and a lower alkyl alcohol to catalytic reaction in the presence of an alkali metal alkoxide catalyst is provided, which process comprises carrying out the catalytic reaction at 50°–400° C., adding a specified ether compound, and which process affords such advantages that the alkali metal alkoxide catalyst well dissolves in the reaction mixture to make it possible to easily carry out the reaction; whether Si-containing particles as raw material for Si are fine or coarse, the reaction can be carried at an increased reaction rate; and the yield of the tetraalkoxysilane per hour per unit weights of raw materials is high.

14 Claims, No Drawings

PROCESS FOR PRODUCING A TETRAALKOXYSILANE

BACKGROUND OF THE INVENTION

1. Field of the Invention

This invention relates to a process for producing a tetraalkoxysilane. More particularly it relates to an improved process for producing a tetraalkoxysilane by subjecting silicon and a lower alkyl alcohol to a catalytic reaction in the presence of an alkali metal alkoxide catalyst.

2. Description of the Related Art

Heretofore, as a commercial production process of tetraalkoxysilanes, there is a process utilizing the dehydrochlorination reaction of SiCl₄ with alcohols. According to the process, however, polymer formation as a side reaction occurs due to a by-product, hydrogen chloride, and also there exists, for example, a problem that steps must be taken for preventing corrosion of reaction equipment due to the presence of hydrogen chloride.

Thus, as a production process of tetraalkoxysilanes having overcome such a problem to a certain extent, there is also known a process of directly reacting silicon with alcohols in the presence of an alkali metal alkoxide. For example, there is known a process of A.Lenz et al using sodium methylate (Japanese patent publication No. 45-8217/1970), a process of W. Flick et al using a compound selected from ether alcohols and alkanolamines (Japanese patent application laid-open No. 54-138523/1979) and a process of Delaval et al using a waste matter powder formed in the direct preparation of methyl (or phenyl) chlorosilane containing at least 30 % of silicon and also using as a diluent, an aromatic hydrocarbon having a boiling point of 190° C. or higher and a melting point of 40° C. or lower (French patent No. 2,332,993).

Now, when a tetraalkoxysilane is produced by reacting silicon with alcohols in the presence of an alkali metal alkoxide, the following conditions are desired:

(1) a condition that the alkali metal alkoxide catalyst is very soluble in the reaction mixture;
(2) a condition that a desired reaction temperature can be maintained;
(3) a condition that a wide range of silicon-containing materials from fine particles to coarse particles can be used as raw material;
(4) a condition that when coarse particles of silicon are used, the reaction rate is not significantly slower as compared with use of fine particles of silicon;
(5) a condition that the yield of the tetraalkoxysilane based on silicon as a raw material is high;
(6) a condition that continuation and termination of the reaction can be controlled; and
(7) a condition that the tetraalkoxysilane can be produced on a commercial scale and preferably continuously.

According to an embodiment of the above process of A. Lenz et al, a 38 % solution (1 Kg) of sodium methylate is added to ferrosilicon in the form of fine particles (silicon, 90 % by weight; particle diameter, about 10 μm), followed by reacting the mixture at 100° C. for 2 hours, so that sodium methylate crystallizes at the final period of the reaction; thus in order to dissolve it, fresh methanol (195 g) is further added. However, according such a process, the solubility of the alkali metal alkoxide in the reaction mixture is low. On the other hand, another embodiment of the process of A. Lenz et al discloses that when the reaction is conducted using a 15 % solution of sodium methylate, addition of fresh methanol at the final period of the reaction after 4 hours is unnecessary, but in order to raise the solubility of the alkali metal alkoxide, a long time is required.

Further, according to still another embodiment of the process of A. Lenz et al, when ferrosilicon in the form of coarse particles (silicon, about 90 % by weight; average particle diameter, about 1 cm) is used, a reaction time as long as 280 hours is required and the use of the sodium methylate catalyst is very large.

On the other hand, according to an embodiment of the above process of W. Flick et al, when purified silicon (Si, 99.8~100% by weight; particle diameter <10μ), tetraethoxysilane, ethanol, sodium ethoxide and ethylglycol are reacted at a reaction temperature of 140° C. to 155° C., the quantity of hydrogen generated is reduced to about 1/20 of that at the initial period of the reaction, so that the reaction temperature must be maintained by gradually reducing the ethanol feed during the progress of the reaction; hence operation is troublesome.

According to an embodiment of the above process of Delaval et al, silicon having a purity of about 72 %, methanol, tetramethoxysilane, sodium methoxide and an aromatic hydrocarbon such as diisopropylbenzene as a diluent are reacted at 120° C. However, according to an experiment of the present inventors, when silicon having a purity of 94 %, methanol, tetramethoxysilane, sodium methoxide and tetralin or dibenzyltoluene as a diluent were reacted, a portion of sodium methoxide adheres to the wall of the reaction vessel together with silicon, and the reaction rate of silicon having an average particle diameter of 100 μm was low (see Comparative examples 1 and 2 mentioned later).

SUMMARY OF THE INVENTION

An object of the present invention is to provide a process for producing a tetraalkoxysilane having overcome the drawbacks of the prior art, wherein the alkali metal alkoxide catalyst is very soluble in the reaction mixture.

Another object of the present invention is to provide a process for producing a tetraalkoxysilane wherein the proportion of the tetraalkoxysilane produced per hour and per unit amount of raw material is high.

The present invention resides in:

A process for producing a tetraalkoxysilane by subjecting silicon and a lower alkyl alcohol to a reaction in the presence of an alkali metal alkoxide catalyst, which process comprises carrying out said reaction adding at least one ether compound in a quantity of 1 to 10,000 parts by weight per 100 parts by weight of silicon, selected from the group consisting of compounds expressed by the formula (I)

$$R^1-O-(X-O)_m-R^2 \tag{I}$$

wherein $R^1$ and $R^2$ each represent a group selected from an alkyl group of 1 to 6 carbon atoms, phenyl group and benzyl group; X represents a linear alkylene group of 2 to 8 carbon atoms which may be substituted by an alkyl group of 1 to 4 carbon atoms, an alkoxy group of 1 to 4 carbon atoms, an alkoxyalkyl group in which each alkoxy and alkyl have 1 to 4 carbon atoms, phenyl group or cyclohexyl group; m represents an integer of 1 to 8, and, in the case m is an integer of 2 to 8, $-(X-O)_m-$ means two or more oxyalkylene groups which may be the same or different with each other and may be substituted by said substituent, combined in m numbers in total, and cyclic ether compounds expressed by the formula (II)

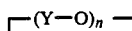 (II)

wherein Y represents a linear alkylene group of 1 to 8 carbon atoms which may be substituted by an alkyl group of 1 to 4 carbon atoms, an alkoxy group of 1 to 4 carbon atoms, an alkoxyalkyl group in which each alkoxy and alkyl have 1 to 4 carbon atoms, n represents an integer of 2 to 10, and —(Y—O)$_n$—means two or more oxyalkylene groups which may be the same or different with each other and may be substituted by said substituent, combined in n numbers in total.

DETAILED DESCRIPTION OF PREFERRED EMBODIMENTS

Examples of silicon used in the present invention are the so-called metallic silicon of a high purity obtained by reducing silica stone, alloys of silicon with other metals represented by iron.

The content of silicon in the metallic silicon and/or silicon-metal alloys is desired to be 80 % by weight or higher, preferably 90 % by weight or higher. Further, the particle diameter of the metallic silicon and/or silicon-metal alloys is preferred to be 1 mm or less.

Examples of the lower alkyl alcohol used in the present invention are alkyl alcohols of 1 to 5 carbon atoms such as methanol, ethanol, i-propanol, n-propanol, n-butanol, i-butanol, and t-butanol, pentanol, 2-methylbutanol, 3-methylbutanol, etc. Among these, methanol is preferred.

As to the lower alkyl alcohol used in the present invention, in order to avoid decomposition of the alkali metal alkoxide and/or tetraalkoxysilane, it is preferred to use those dehydrated with a drying agent represented by calcium chloride, zeolite, aluminum chloride, anhydrous sodium sulfate, anhydrous magnesium sulfate, silica gel, and molecular sieves.

Examples of the alkali metal alkoxide catalyst are lithium, sodium, potassium, rubidium, etc.

As to the alkali metal alkoxides, those having the same kind of alkyl group as that of the lower alkyl alcohol are usually selectively used, but those having a different kind of alkyl group from that of the lower alkyl group may also be used.

As to the alkali metal alkoxide, those prepared separately may be used as they are, and may be used in the form of a solution or suspension of the alkali metal alkoxide and the lower alkyl alcohol. Further, silicon and the lower alkyl alcohol may be reacted in advance in a reaction vessel to prepare the alkali metal alkoxide, which may be then used as it is.

The ether compound used in the present invention include those having a basic skeleton part of a linear or cyclic polyoxyalkylene chain, expressed by the above-mentioned formula (I) or (II).

Examples of the ether compound expressed by the formula (I) are ethylene glycol dimethyl ether, ethylene glycol dipropyl ether, ethylene glycol dibutyl ether, trimethylene glycol dibutyl ether, tetramethylene glycol dibutyl ether, diethylene glycol dimethyl ether, diethylene glycol diethyl ether, diethylene glycol dibutyl ether, diethylene glycol benzyl methyl ether, triethylene glycol dimethyl ether, triethylene glycol ethyl methyl ether, tetraethylene glycol dimethyl ether, tetraethylene glycol diethyl ether, tetraethylene glycol dibutyl ether, pentamethylene glycol dimethyl ether, pentaethylene glycol dimethyl ether, 1,2,3-tributoxypropane, 2,2-bis(methoxymethyl)-1,3-dimethoxypropane, 2,2-dimethyl-1,3-dimethoxypropane, etc.

Among these, lower alkyl ethers of polyethylene glycol are preferred and diethylene glycol dimethyl ether and triethylene glycol dimethyl ether are particularly preferred.

Examples of the ether linkage-containing compound expressed by the formula (II) are 1,3-dioxane, 1,4-dioxane, 1,4-benzodioxane, 1,4,7,10-tetraoxacyclododecane (another name: 12-crown ether-4), 1,4,7,10,13-pentaoxacyclopentadecane (another name: 15-crown ether-15), 1,4,7,10,13,16-hexaoxacyclooctandecane (another name: 18-crown ether-6), 2,3,11,12-dibenzo-1,4,7,10,13,16-hexaoctacyclooctadecane-2,11-diene (another name: dibenzo-18-crown ether-6), 2,3,11,12-dicyclohexano-1,4,7,10,13,16-hexaoctacyclooctadecane (another name: dicyclohexano-18-crown ether-6), 2,3,14,15-dicyclohexano-1,4,7,10,13,16,19,22-octaoxacyclotetracosane (another name: dicyclohexano-24-crown ether-8), etc.

Among these, crown ethers are preferred and 12-crown ether-4 is particularly preferred.

As to the ether compounds, commercially available products may be used, or those prepared as follows may be used:

For example, according to Williamson's synthesis method, NaOMe is reacted with the —OH group of an alcohol to obtain a compound having a —ONa group, which is then reacted with a halogenated hydrocarbon RX to prepare an ether compound having an alkoxy group—OR. As for another method, an ether compound having an alkoxy group—OR can be obtained by the dehydration reaction of an ether having an—OH group with an alcohol having the—OH group.

The reaction of the present invention may be carried out either batchwise or continuously. The batchwise reaction is preferred to be carried out by introducing silicon, an alkali metal alkoxide and an ether compound into a reaction vessel, heating the inside of the reaction vessel to a definite temperature and thereafter carrying out the reaction while dropwise adding a lower alkyl alcohol to the reaction vessel.

Further, a continuous, reaction may be carried out by successively adding raw material silicon to the reaction vessel in accordance with the quantity of silicon consumed by the reaction and also supplementing the quantities of raw material silicon, the catalyst and the ether compound corresponding to those which have been withdrawn from the reaction vessel and reduced as much.

In either of the batchwise or the continuous reaction, it is possible to add, in advance, a certain quantity of a tetraalkoxysilane to the reaction system at the time of initiating the reaction to thereby initiate the reaction rapidly.

In the present invention, it is possible to use silicon, the lower alkyl alcohol, the alkali metal alkoxide and the ether compound in the following proportions:

The proportions of quantities of silicon and the lower alkyl alcohol added may be theoretically stoichiometric, but usually the quantity of the lower alkyl alcohol fed is 4 to 20 mols per one gram atom of silicon contained in the silicon-containing material consumed by the reaction. However, the lower alkyl alcohol may be added in excess of silicon, or to the contrary, silicon may be added in excess of the lower alkyl alcohol. Further, the lower alkyl alcohol may be provided in a small quantity at the time of initiating the reaction and its quantity may then be gradually increased up to the above-mentioned proportion.

The quantity of the alkali metal alkoxide added may be 0.1 to 100 parts by weight, preferably 1 to 20 parts by weight per 100 parts by weight of the ether compound. If the quantity is less than the above lower limit of the range, the reaction proceeds with difficulty, while if it exceeds the upper limit, not only does the cost increase, but also solubility problems may occur.

Further, the quantity of the ether compound added may be 1 to 10,000 parts by weight, preferably 100 to 5,000 parts by weight, per 100 parts by weight of raw material silicon. If the quantity is less than the lower limit of the range, its effectiveness cannot be expected, while if it exceeds the upper limit, the effectiveness meeting with the increase of the quantity cannot be exhibited and hence such an excess quantity is meaningless.

The reaction temperature may be in the range of 50° to 400° C., but in order to raise the reaction rate, it is preferred to carry out the reaction at 100° C. or higher. By raising the reaction temperature to a suitable one and distilling off the thus formed tetraalkoxysilane and unreacted lower alkyl alcohol from the reaction vessel, it is possible to keep the volume of the reaction mixture at a nearly constant one. By distilling the resulting distillate, it is possible to separate the tetraalkoxysilane having an elevated purity and at the same time it is possible to recover unreacted lower alkyl alcohol. Further, in the case where the ether compound is contained in the distillate, it is possible to recover the ether compound by distillation. The recovered lower alkyl alcohol and the ether compound thus recovered may be recirculated to the reaction vessel for reuse.

In the process of the present invention, the reaction pressure may be atmospheric and if necessary, an elevated pressure or a reduced pressure.

The thus produced tetraalkoxysilane can be suitably used, for example, as an additive for preventing coarse holes in concrete, cement, etc., a binding agent for molding sand, a material for coating the surface of glass or metal together with various kinds of polymers, etc. and further it may be hydrolyzed and can be suitably used as the raw material for producing silicon dioxide of a high purity.

The effectiveness exhibited by the present invention is as follows:

(1) By adding a specified ether compound, the alkali metal alkoxide dissolves well in the reaction mixture; deposition of the alkali metal alkoxide and its adhesion to the wall of the reaction vessel during the reaction are prevented; and it is possible to raise the reaction rate.

(2) By selecting a high boiling ether compound, it is possible to carry out the reaction at high temperatures. For example, in the case where methanol having a boiling point of 65° C. is used as a raw alcohol, it is possible to maintain the reaction temperature at about 120° C. by selecting triethylene glycol dimethyl ether as an ether compound.

(3) By distilling off continuously the formed tetraalkoxysilane in the reaction mixture together with unreacted lower alkyl alcohol therein during the reaction, it is possible to easily recover these compounds.

(4) As to the silicon used in the present invention, those having a relatively large particle diameter can be used; hence it is possible to simplify the operations of grinding and classifying the silicon.

(5) The yield of the tetraalkoxysilane relative to the silicon used is high, and the quantity of by-products other than hydrogen is neglegibly small.

(6) In the case where the reaction is carried out by continuously feeding a lower alkyl alcohol to the reaction system, it is possible to discontinue or restart the reaction by discontinuing or restarting the feed of the lower alkyl alcohol.

(7) By continuously feeding silicon and a lower alkyl alcohol to the reaction system and distilling off the resulting tetraalkoxysilane, etc. from the reaction system, it is possible to continuously commercially produce the tetraalkoxysilane.

The present invention will be described in more detail by way of Examples and Comparative examples, but it should not be construed to be limited thereto.

EXAMPLE 1

A continuous reaction was carried out in a stainless steel reaction vessel having about 40% capacity and equipped with a silicon-supply pipe, an alcohol-supply pipe, a vapor-distillation pipe having a condenser fitted thereto, a stirrer and a thermocouple thermometer.

Silicon (2.13 Kg; purity 94% by weight; pure silicon content 2.00 Kg) having a nominal median diameter (particle diameter of 50% by weight accumulated particles) of 20 μm, triethylene glycol dimethyl ether (9.00 Kg) and tetramethoxysilane (0.49 Kg) were introduced to the above reaction vessel and the contents were heated to 125° C. with stirring, followed by dropwise addition of a methanol solution (2.50 Kg) of sodium methoxide (0.7 Kg) into the reaction vessel. After completion of the dropwise addition, generation of hydrogen gas was observed.

A suspension of silicon in methanol (water content: 300 ppm) was then continuously fed to the reaction vessel and the reaction was continued while the temperature of the reaction mixture was kept at 120°–125° C. The thus formed tetramethoxysilane together with methanol were distilled off.

The quantity of hydrogen generated per unit time was nearly constant during the reaction. After 45.9 hours, feed and heating of silicon and methanol were stopped. Silicon (about 2 Kg) remained in the reaction vessel.

The resulting distillate and cooled reaction mixture were analyzed by gas chromatography. The results are shown in Table 1.

EXAMPLE 2

Example 1 was repeated except that reaction was carried out for 61.5 hours, using silicon (purity: about 94 % by weight, nominal mediam diameter: 35 μm (a material having passed through 100 mesh sieve (mesh opening corresponding to 0.149 mm)). The results are shown in Table 1.

TABLE 1

| | Raw materials | | | Tetramethoxysilane | | |
|---|---|---|---|---|---|---|
| | Nominal median diameter of metallic silicon Dmed (μm) | Feeding rate of metallic silicon (Kg/hr) | Feeding rate of methanol (Kg/hr) | Reaction time (hr) | Amount formed (Kg) | Yield based on metallic silicon fed (%) | Yield based on methanol (%) |
| Example 1 | 20 | 0.534 | 4.06 | 45.9 | 126.0 | 87.0 | 56.9 |
| Example 2 | 35 | 0.143 | 1.23 | 61.5 | 47.6 | 80.5 | 51.9 |

EXAMPLES 3~8

Into a 500 ml capacity glass flask equipped with an alcohol-supply tube, a vapor-distillation tube having a condenser fitted thereto, a stirrer and a thermometer were introduced silicon (25 g) having various purities and nominal median diameters shown in Table 2, a 28% methanol solution (28 g) of sodium methoxide and various kinds of ether compounds (50 g) shown in Table 2. The mixture in the flask was heated to 125° C. with stirring, followed by continuously feeding methanol (water content: 300 ppm) at an addition rate of 0.33 ml/min to carry out batchwise reaction.

Generation of hydrogen gas in the flask was observed, and the resulting tetramethoxysilane together with unreacted methanol were distilled off while the temperature of the reaction mixture was kept at 115°~125° C. In the respective experiments, the quantity of hydrogen generated decreased gradually, accompanying the progress of the reaction. During the reaction, there was no adhesion of sodium methoxide, etc. to the wall of the flask.

After completion of the reaction, the distillate and the reaction mixture were analyzed by gas chromatography. The results are shown in Table 2. In this Table, silicon having a nominal median diameter of 100 μm corresponds to 60 mesh (mesh opening corresponding to 0.250 mm) pass and 200 mesh (mesh opening corresponding to 0.074 mm) on.

COMPARATIVE EXAMPLES 1 and 2

Examples 3~8 were repeated except that using silicon (25 g) (the same as in Examples 6~8) having a purity and a nominal median diameter shown in Table 2, the ether compounds used in Examples 3~8 were replaced by tetralin or dibenzyl toluene. Solids containing sodium methoxide and silicon adhered to the inner wall of the reaction vessel. The results of the reaction are shown in Table 2.

EXAMPLE 9

A batchwise reaction was carried out in the same manner as in Example 6.

After reaction was continued for 3 hours, heating and methanol feed were stopped. When 24 hours lapsed after the discontinuation of the reaction, the inside of the flask was heated to 125° C. and methanol feed was restarted. As a result, generation of hydrogen in the flask was observed. The quantity of hydrogen generated per unit time before the discontinuation of the reaction was almost the same as that after restarting the reaction.

When 6.9 hours lapsed after restarting the reaction, heating and methanol feed were stepped. The distillate and cooled reaction mixture were analyzed by gas chromatography. As a result, the quantity of tetramethoxysilane formed was 53.5 g. Thus, in the process of the present invention, it is possible to easily discontinue and restart the reaction.

TABLE 2

| | Metallic Si | | | | Tetramethoxysilane | |
|---|---|---|---|---|---|---|
| | Nominal median diameter Dmed (μm) | Purity (wt %) | Ether linkage-containing compound or hydrocarbon (g) | Reaction time (hr) | Amount formed (g) | yield based on metallic Si fed (%) |
| Example 3 | 10.5 | 99 | Triethylene glycol dimethyl ether 50 | 7.3 | 121.1 | 89.1 |
| Example 4 | 22 | 99 | Triethylene glycol dimethyl ether 50 | 7.6 | 104.0 | 76.6 |
| Example 5 | 40 | 99 | Triethylene glycol dimethyl ether 50 | 7.5 | 63.1 | 46.4 |
| Example 6 | 100 | 94 | Triethylene glycol dimethyl ether 50 | 9.9 | 53.6 | 39.4 |
| Example 7 | 100 | 94 | Diethylene glycol dimethyl ether 50 | 11.4 | 16.5 | 34.3 |
| Example 8 | 100 | 94 | 12-Crown ether-4 50 | 7.0 | 50.3 | 37.1 |
| Comp. ex. 1 | 100 | 94 | Tetralin 50 | 11.5 | 33.4 | 24.0 |
| Comp. ex. 2 | 100 | 94 | Dibenzyltoluene 50 | 9.0 | 29.1 | 21.4 |

What we claim is:

1. A process for producing a tetraalkoxysilane by subjecting silicon and a lower alkyl alcohol to a reaction in the presence of an alkali metal alkoxide catalyst, which process comprises adding at least one ether compound in a quantity quantity of 1 to 10,000 parts by weight per 100 parts by weight of silicon, selected from the group consisting of compounds expressed by the formula (I)

$$R^1 - O - (X - O)_m - R^2 \qquad (I)$$

wherein R¹ and R² each represent a group selected from an alkyl group of 1 to 6 carbon atoms, phenyl group and benzyl group; X represents a linear alkylene group of 2 to 8 carbon atoms which may be substituted by an alkyl group of 1 to 4 carbon atoms, an alkoxy group of 1 to 4 carbon atoms, an alkoxy alkyl group in which each alkoxy and alkyl have 1 to 4 carbon atoms, phenyl group or cyclohexyl group; m represents an integer of 1 to 8, and, in the case m is an integer of 2 to 8, $-(X-O)_m-$ means two or more oxyalkylene groups which may be the same or different from each other and may be substituted by said substituent, combined in m numbers in total, and cyclic ether compounds expressed by the formula (II)

$$\boxed{-(Y-O)_n-} \quad (II)$$

wherein Y represents a linear alkylene group of 1 to 8 carbon atoms which may be substituted by an alkyl group of 1 to 4 carbon atoms, an alkoxy group of 1 to 4 carbon atoms, an alkoxyalkyl group in which each alkoxy and alkyl have 1 to 4 carbon atoms, n represents an integer of 2 to 10, and $-(Y-O)_n-$ means two or more oxyalkylene groups which may be the same or different from each other and may be substituted by said substituent, combined in n numbers in total.

2. A process for producing a tetraalkoxysilane according to claim 1 wherein said ether compound is expressed by said formula (I); R¹ and R² each represent an alkyl group of 1 to 4 carbon atoms; X represents a linear alkylene group of 2 to 5 carbon atoms; and m represents an integer of 1 to 5.

3. A process for producing a tetraalkoxysilane according to claim 2 wherein said ether compound is diethylene glycol dimethyl ether.

4. A process for producing a tetraalkoxysilane according to claim 2 wherein said ether compound is triethylene glycol dimethyl ether.

5. A process for producing a tetraalkoxysilane according to claim 1 wherein said ether compound is expressed by said formula (II); said Y represents a linear alkylene group of 1 to 3 carbon atoms.

6. A process for producing a tetraalkoxysilane according to claim 1 wherein said ether compound is expressed by said formula (II); said Y represents—CH₂—CH₂—group and n represents an integer of 2 to 6.

7. A process for producing a tetraalkoxysilane according to claim 5 wherein said ether compound is expressed by said formula (II); said Y represents—CH₂—CH₂—group and n represents an integer of 2 to 6.

8. A process for producing a tetraalkoxysilane according to claim 5 wherein said ether compound is 1,4,7,10-tetraoxacyclododecane.

9. A process for producing a tetraalkoxysilane according to claim 1 wherein said ether compound is added in a quantity of 100 to 5,000 parts by weight per 100 parts by weight of silicon.

10. A process for producing a tetraalkoxysilane according to claim 1 wherein an alkaline metal alkoxide is used in a quantity of 0.1 to 100 parts by weight per 100 parts by weight of said ether compound.

11. A process for producing a tetraalkoxysilane according to claim 1 wherein said lower alkyl alcohol is used in a quantity of 4 to 20 mols per one gram atom of silicon.

12. A process for producing a tetraalkoxysilane according to claim 1 wherein said reaction temperature is in the range of 50 to 400° C.

13. A process for producing a tetraalkoxysilane according to claim 1 wherein said lower alkyl alcohol is methyl alcohol.

14. A process for producing a tetraalkoxysilane according to claim 1 wherein said lower alkyl alcohol is methyl alcohol; said alkali metal alkoxide is sodium methoxide; and silicon and methyl alcohol are subjected to a catalytic reaction at a temperature of 100° C. to 200° C.

* * * * *

UNITED STATES PATENT AND TRADEMARK OFFICE
CERTIFICATE OF CORRECTION

PATENT NO.  :  4,752,647
DATED       :  June 21, 1988
INVENTOR(S) :  Inaba et al.

It is certified that error appears in the above-identified patent and that said Letters Patent is hereby corrected as shown below:

Column 6, line 31, change "40%" to --40ℓ--.

Signed and Sealed this

Seventeenth Day of January, 1989

Attest:

DONALD J. QUIGG

*Attesting Officer*   *Commissioner of Patents and Trademarks*